United States Patent [19]

Sih

[11] 4,398,025

[45] Aug. 9, 1983

[54] 2-DECARBOXY-2-TETRAZOLYL-19-HYDROXY-PG COMPOUNDS

[75] Inventor: John C. Sih, Kalamazoo, Mich.

[73] Assignee: The Upjohn Company, Kalamazoo, Mich.

[21] Appl. No.: 337,649

[22] Filed: Jan. 7, 1982

Related U.S. Application Data

[60] Continuation of Ser. No. 88,499, Oct. 26, 1979, abandoned, which is a division of Ser. No. 25,899, Apr. 2, 1979, Pat. No. 4,228,104.

[51] Int. Cl.³ .......................................... C07D 257/04
[52] U.S. Cl. ................................... 542/429; 548/253
[58] Field of Search ................ 548/253; 542/426, 429

[56] References Cited

U.S. PATENT DOCUMENTS

| | | | |
|---|---|---|---|
| 3,657,316 | 4/1972 | Samuelsson | 544/107 X |
| 3,922,297 | 11/1975 | Pike | 544/107 |
| 4,024,179 | 5/1977 | Bindra et al. | 598/253 X |

OTHER PUBLICATIONS

Nelson et al., C & EN Aug. 16, 1982, p. 41.

*Primary Examiner*—Mark L. Berch
*Assistant Examiner*—D. B. Springer
*Attorney, Agent, or Firm*—Lawrence T. Welch; Robert A. Armitage

[57] ABSTRACT

The present invention provides novel 2-decarboxy-2-hydroxymethyl-19,20-didehydro-13,14-dihydro-$PG_1$ compounds methods for their preparation and pharmacological use for the induction of prostaglandin-like effect.

1 Claim, No Drawings

2-DECARBOXY-2-TETRAZOLYL-19-HYDROXY-PG COMPOUNDS

CROSS REFERENCE TO RELATED APPLICATIONS

This is a continuation of application Ser. No. 88,499, filed Oct. 26, 1979, abandoned, which is a division of Ser. No. 025,899, filed Apr. 2, 1979, U.S. Pat. No. 4,228,104.

BACKGROUND OF THE INVENTION

The present invention relates to novel prostaglandin analogs. Particularly, these compounds are analogs of the prostaglandins wherein the C-19 position is substituted by hydroxy, i.e., 19-hydroxy-PG compounds. Most particularly, the present invention relates to novel 2-decarboxy-2-tetrazolyl-19-hydroxy-PG compounds, a disclosure of the preparation and use of which is incorporated here by reference from U.S. Ser. No. 025,899, filed Apr. 2, 1979.

PRIOR ART

Prostaglandin analogs exhibiting hydroxylation in the 19-position are known in the art. See, for example, U.S. Pat. No. 4,127,612, Sih, J. C., Prostaglandins 13:831 (1977) and U.S. Pat. Nos. 3,657,316, 3,878,046, and 3,922,297. See also the additional references cited in U.S. Ser. No. 025,899.

SUMMARY OF THE INVENTION

The present invention particularly provides:
A compound of the formula

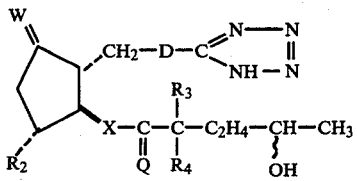

wherein D is
 (1) cis—$CH=CH-CH_2-(CH_2)_g-CH_2-$,
 (2) cis—$CH=CH-CH_2-(CH_2)_g-CF_2-$,
 (3) cis—$CH_2-CH=CH-CH_2-CH_2-$,
 (4) trans—$(CH_2)_3-CH=CH-$,
 (5) —$(CH_2)_3-(CH_2)_g-CH_2-$,
 (6) —$(CH_2)_3-CH_2-CF_2-$,
 (7) —$(CH_2)_3-O-CH_2-$,
 (8) —$(CH_2)_2-O-(CH_2)_2-$,
 (9) —$CH_2-O-(CH_2)_3-$,
 (10) —(m—ph)—$(CH_2)_2-$, or
 (11) —(m—ph)—O—$CH_2-$
wherein m—ph is inter-meta-phenylene, and
wherein g is zero, one, two or three;
 wherein Q is $\alpha-OH:\beta-R_5$ or $\alpha-R_5:\beta-OH$,
 wherein $R_5$ is hydrogen or methyl,
wherein $R_2$ is hydrogen, hydroxyl, or hydroxymethyl;
wherein $R_3$ and $R_4$ are hydrogen, methyl, or fluoro, being the same or different, with the proviso that one of $R_3$ and $R_4$ is fluoro only when the other is hydrogen or fluoro;
wherein W is oxo, methylene, $\alpha-OH:\beta-H$, or $\alpha-H:\beta-OH$;
 and wherein X is cis— or trans—$CH=CH-$, —$C\equiv C-$, or —$CH_2CH_2-$.

With regard to the divalent the substituents described above (e.g., Q) these divalent radicals are defined as $\alpha-R_I:\beta-R_J$, wherein $R_I$ represents the substituent of the divalent moiety in the alpha configuration with respect to the ring and $R_J$ represents the substituent of the divalent moiety in the beta configuration with respect to the plane of the ring. Accordingly, when Q is defined as $\alpha-OH:\beta-R_5$, the hydroxy of the Q moiety is in the alpha configuration, i.e., as in the natural prostaglandin, and the $R_5$ substituent is in the beta configuration.

Specific embodiments of the present invention include:
2-decarboxy-2-tetrazolyl-19(R)-19-hydroxyPGF$_{2\alpha}$,
2-decarboxy-2-tetrazolyl-11-deoxy-19(R)-19-hydroxy-PGF$_{2\alpha}$,
2-decarboxy-2-tetrazolyl-11-deoxy-11α-hydroxymethyl-19(R)-19-hydroxy-PGF$_{2\alpha}$,
2-decarboxy-2-tetrazolyl-19(R)-19-hydroxy-PGF$_{2\beta}$,
2-decarboxy-2-tetrazolyl-11-deoxy-19(R)-hydroxy-PGF$_{2\beta}$,
2-decarboxy-2-tetrazolyl-11-deoxy-11α-hydroxymethyl-19(R)-19-hydroxy-PGF$_{2\beta}$,
2-decarboxy-2-tetrazolyl-19(R)-19-hydroxy-PGE$_2$,
2-decarboxy-2-tetrazolyl-11-deoxy-19(R)-19-hydroxy-PGE$_2$,
2-decarboxy-2-tetrazolyl-11-deoxy-11α-hydroxymethyl-19(R)-19-hydroxy-PGE$_2$,
2-decarboxy-2-tetrazolyl-9-deoxo-9-methylene-19(R)-19-hydroxy-PGE$_2$,
2-decarboxy-2-tetrazolyl-9-deoxo-9-methylene-11-deoxy-19(R)-19-hydroxy-PGE$_2$,
2-decarboxy-2-tetrazolyl-9-deoxo-9-methylene-11-deoxy-11α-hydroxymethyl-19(R)-19-hydroxy-PGE$_2$,
2-decarboxy-2-tetrazolyl-4,5-didehydro-19(R)-19-hydroxy-PGF$_{1\alpha}$,
2-decarboxy-2-tetrazolyl-4,5-didehydro-19(R)-19-hydroxy-15(S)-15-methyl-PGF$_{1\alpha}$,
2-decarboxy-2-tetrazolyl-4,5,13,14,-tetradehydro-19(R)-19-hydroxy-PGF$_{1\alpha}$,
2-decarboxy-2-tetrazolyl-4,5,13,14-tetradehydro-19(R)-19-hydroxy-16,16-difluoro-PGF$_{1\alpha}$,
2-decarboxy-2-tetrazolyl-4,5-didehydro-19(R)-19-hydroxy-11-deoxy-PGF$_{1\alpha}$,
2-decarboxy-2-tetrazolyl-4,5-didehydro-19(R)-19-hydroxy-11-deoxy-15(S)-15-methyl-PGF$_{1\alpha}$,
2-decarboxy-2-tetrazolyl-4,5,13,14-tetradehydro-19(R)-19-hydroxy-11-deoxy-PGF$_{1\alpha}$,
2-decarboxy-2-tetrazolyl-4,5,13,14-tetradehydro-19(R)-19-hydroxy-11-deoxy-16,16-difluoro-PGF$_{1\alpha}$,
2-decarboxy-2-tetrazolyl-4,5-dideoxy-19(R)-19-hydroxy-11-deoxy-11α-hydroxymethyl-PGF$_{1\alpha}$,
2-decarboxy-2-tetrazolyl-4,5-dideoxy-19(R)-19-hydroxy-11-deoxy-11α-hydroxymethyl-15(S)-15-methyl-PGF$_{1\alpha}$,
2-decarboxy-2-tetrazolyl-4,5,13,14-tetradehydro-19(R)-19-hydroxy-11-deoxy-11α-hydroxymethyl-PGF$_{1\alpha}$,
2-decarboxy-2-tetrazolyl-4,5,13,14-tetradehydro-19(R)-19-hydroxy-11-deoxy-11α-hydroxymethyl-16,16-difluoro-PGF$_{1\alpha}$,
2-decarboxy-2-tetrazolyl-4,5-didehydro-19(R)-19-hydroxy-PGF$_{1\beta}$,
2-decarboxy-2-tetrazolyl-4,5-didehydro-19(R)-19-hydroxy-15(S)-15-methyl-PGF$_{1\beta}$,
2-decarboxy-2-tetrazolyl-4,5,13,14-tetradehydro-19(R)-19-hydroxy-PGF$_{1\beta}$,
2-decarboxy-2-tetrazolyl-4,5,13 14-tetradehydro-19(R)-19-hydroxy-16,16-difluoro-PGF$_{1\beta}$, 2-decarboxy-2-tetrazolyl-4,5-didehydro-19(R)-19-hydroxy-11-deoxy-PGF$_{1\beta}$,
2-decarboxy-2-tetrazolyl-4,5-didehydro-19(R)-19-hydroxy-11-deoxy-15(S)-methyl-PGF$_{1\beta}$,
2-decarboxy-2-tetrazolyl-4,5,13,14-tetradehydro-19(R)-19-hydroxy-11-deoxy-PGF$_{1\beta}$,
2-decarboxy-2-tetrazolyl-4,5,13,14-tetradehydro-19(R)-19-hydroxy-11-deoxy-16,16-difluoro-PGF$_{1\beta}$,
2-decarboxy-2-tetrazolyl-4,5-didehydro-19(R)-19-hydroxy-11-deoxy-11α-hydroxymethyl-PGF$_{1\beta}$,
2-decarboxy-2-tetrazolyl-4,5-didehydro-19(R)-19-hydroxy-11-deoxy-11α-hydroxymethyl-15(S)-15-methyl-PGF$_{1\beta}$,
2-decarboxy-2-tetrazolyl-4,5,13,14-tetradehydro-19(R)-19-hydroxy-11-deoxy-11α-hydroxymethyl-PGF$_{1\beta}$,
2-decarboxy-2-tetrazolyl-4,5,13,14-tetradehydro-19(R)-19-hydroxy-11-deoxy-11α, hydroxymethyl-16,16-difluoro-PGF$_{1\beta}$,
2-decarboxy-2-tetrazolyl-4,5-didehydro-19(R)-19-hydroxy-PGE$_1$,
2-decarboxy-2-tetrazolyl-4,5-didehydro-19(R)-19-hydroxy-15(S)-15-methyl-PGE$_1$,
2-decarboxy-2-tetrazolyl-4,5,13,14-tetradehydro-19(R)-19-hydroxy-PGE$_1$,
2-decarboxy-2-tetrazolyl-4,5,13,14-tetradehydro-19(R)-19-hydroxy-16,16-difluoro-PGE$_1$.
2-decarboxy-2-tetrazolyl-4,5-didehydro-19(R)-19-hydroxy-11-deoxy-PGE$_1$,
2-decarboxy-2-tetrazolyl-4,5-didehydro-19(R)-19-hydroxy-11-deoxy-15(S)-15-methyl-PGE$_1$,
2-decarboxy-2-tetrazolyl-4,5,13,14-tetradehydro-19(R)-19-hydroxy-11-deoxy-PGE$_1$,
2-decarboxy-2-tetrazolyl-4,5,13,14-tetradehydro-19(R)-19-hydroxy-11-deoxy-16,16-difluoro-PGE$_1$,
2-decarboxy-2-tetrazolyl-4,5-didehydro-19(R)-19-hydroxy-11-deoxy-11α-hydroxymethyl-PGE$_1$,
2-decarboxy-2-tetrazolyl-4,5-didehydro-19(R)-19-hydroxy-11-deoxy-11α-hydroxymethyl-15(S)-15-methyl-PGE$_1$,
2-decarboxy-2-tetrazolyl-4,5,13,14-tetradehydro-19(R)-19-hydroxy-11-deoxy-11α-hydroxymethyl-PGE$_1$,
2-decarboxy-2-tetrazolyl-4,5,13,14-tetradehydro-19(R)-19-hydroxy-11-deoxy-11α-hydroxymethyl-16,16-difluoro-PGE$_1$,
2-decarboxy-2-tetrazolyl-4,5-didehydro-19(R)-19-hydroxy-9-deoxo-9-methylene-PGE$_1$,
2-decarboxy-2-tetrazolyl-4,5-didehydro-19(R)-19-hydroxy-9-deoxo-9-methylene-15(S)-15-methyl-PGE$_1$,
2-decarboxy-2-tetrazolyl-4,5,13,14-tetradehydro-19(R)-19-hydroxy-9-deoxo-9-methylene-PGE$_1$,
2-decarboxy-2-tetrazolyl-4,5,13,14-tetradehydro19(R)-19-hydroxy-9-deoxo-9-methylene-16,16-difluoro-PGE$_1$,
2-decarboxy-2-tetrazolyl-4,5-didehydro-19(R)-19-hydroxy-9-deoxo-9-methylene-11-deoxy-PGE$_1$,
2-decarboxy-2-tetrazolyl-4,5-didehydro-19(R)-19-hydroxy-9-deoxo-9-methylene-15(S)-15-methyl-PGE$_1$,
2-decarboxy-2-tetrazolyl-4,5,13,14-tetradehydro-19(R)-19-hydroxy-9-deoxo-9-methylene-11-deoxy-PGE$_1$,
2-decarboxy-2-tetrazolyl-4,5,13,14-tetradehydro-19(R)-19-hydroxy-9-deoxo-9-methylene-11-deoxy-16,16-difluoro-PGE$_1$,
2-decarboxy-2-tetrazolyl-4,5-didehydro-19(R)-19-hydroxy-9-deoxo-9-methylene-11-deoxy-11α-hydroxymethyl-PGE$_1$,
2-decarboxy-2-tetrazolyl-4,5-didehydro-19(R)-19-hydroxy-9-deoxo-9-methylene-11-deoxy-11α-hydroxymethyl-15(S)-15-methyl-PGE$_1$,
2-decarboxy-2-tetrazolyl-4,5,13,14-tetradehydro-19(R)-19-hydroxy-9-deoxo-9-methylene-11-deoxy-11α-hydroxy-methyl-PGE$_1$,
2-decarboxy-2-tetrazolyl-4,5,13,14-tetradehydro-19(R)-19-hydroxy-9-deoxo-9-methylene-11-deoxy-11α-hydroxymethyl-16,16-difluoro-PGE$_1$,
2-decarboxy-2-tetrazolyl-2,3-didehydro-19(R)-19-hydroxy-PGF$_{1\alpha}$,
2-decarboxy-2-tetrazolyl-2,3-didehydro-19(R)-19-hydroxy-16,16-difluoro-PGF$_{1\alpha}$,
2-decarboxy-2-tetrazolyl-2,3-didehydro-19(R)-19-hydroxy-15(S)-15-methyl-PGF$_{1\alpha}$,
2-decarboxy-2-tetrazolyl-2,3-didehydro-19(R)-19-hydroxy-11-deoxy-PGF$_{1\alpha}$,
2-decarboxy-2-tetrazolyl-2,3-didehydro-19(R)-19-hydroxy-11-deoxy-16,16-difluoro-PGF$_{1\alpha}$,
2-decarboxy-2-tetrazolyl-2,3-didehydro-19(R)-19-hydroxy-11-deoxy-15(S)-15-methyl-PGF$_{1\alpha}$,
2-decarboxy-2-tetrazolyl-2,3-didehydro-19(R)-19-hydroxy-11-deoxy-11α-hydroxymethyl-PGF$_{1\alpha}$,
2-decarboxy-2-tetrazolyl-2,3-didehydro-19(R)-19-hydroxy-11-deoxy-11α-hydroxymethyl-16,16-difluoro-PGF$_{1\alpha}$,
2-decarboxy-2-tetrazolyl-2,3-didehydro-19(R)-19-hydroxy-11-deoxy-11α-hydroxymethyl-15(S)-15-methyl-PGF$_{1\alpha}$,
2-decarboxy-2-tetrazolyl-2,3-didehydro-19(R)-19-hydroxy-PGF$_{1\alpha}$,
2-decarboxy-2-tetrazolyl-2,3-didehydro-19(R)-19-hydroxy-16,16-difluoro-PGF$_{1\beta}$,
2-decarboxy-2-tetrazolyl-2,3-didehydro-19(R)-19-hydroxy-15(S)-methyl-PGF$_{1\beta}$,
2-decarboxy-2-tetrazolyl-2,3-didehydro-19(R)-19-hydroxy-11-deoxy-PGF$_{1\beta}$,
2-decarboxy-2-tetrazolyl-2,3-didehydro-19(R)-19-hydroxy-11-deoxy-16,16-difluoro-PGF$_{1\beta}$,
2-decarboxy-2-tetrazolyl-2,3-didehydro-19(R)-19-hydroxy-11-deoxy-15(S)-15-methyl-PGF$_{1\beta}$,
2-decarboxy-2-tetrazolyl-2,3-didehydro-19(R)-19-hydroxy-11-deoxy-11α-hydroxymethyl-PGF$_{1\beta}$,
2-decarboxy-2-tetrazolyl-2,3-didehydro-19(R)-19-hydroxy-11-deoxy-11α-hydroxymethyl-16,16-difluoro-PGF$_{1\beta}$,
2-decarboxy-2-tetrazolyl-2,3-didehydro-19(R)-19-hydroxy-11-deoxy-11α-hydroxymethyl-15(S)-15-methyl-PGF$_{1\beta}$,
2-decarboxy-2-tetrazolyl-2,3-didehydro-19(R)-19-hydroxy-PGE$_1$,
2-decarboxy-2-tetrazolyl-2,3-didehydro-19(R)-19-hydroxy-16,16-difluoro-PGE$_1$,
2-decarboxy-2-tetrazolyl-2,3-didehydro-19(R)-19-hydroxy-15(S)-15-methyl-PGE$_1$,
2-decarboxy-2-tetrazolyl-2,3-didehydro-19(R)-19-hydroxy-11-deoxy-PGE$_1$,
2-decarboxy-2-tetrazolyl-2,3-didehydro-19(R)-19-hydroxy-11-deoxy-16,16-difluoro-PGE$_1$,
2-decarboxy-2-tetrazolyl-2,3-didehydro-19(R)-19-hydroxy-11-deoxy-15(S)-15-methyl-PGE$_1$,
2-decarboxy-2-tetrazolyl-2,3-didehydro-19(R)-19-hydroxy-11-deoxy-11α-hydroxymethyl-PGE$_1$,
2-decarboxy-2-tetrazolyl-2,3-didehydro-19(R)-19-hydroxy-11-deoxy-11α-hydroxymethyl-16,16-difluoro-PGE$_1$, 2-decarboxy-2-tetrazolyl-2,3-didehydro-19(R)-19-hydroxy-11-deoxy-11α-hydroxymethyl-15(S)-15-methyl-PGE$_1$,
2-decarboxy-2-tetrazolyl-2,3-didehydro-19(R)-19-hydroxy-9-deoxo-9-methylene-PGE$_1$,
2-decarboxy-2-tetrazolyl-2,3-didehydro-19(R)-19-hydroxy-9-deoxo-9-methylene-16,16-difluoro-PGE$_1$,
2-decarboxy-2-tetrazolyl-2,3-didehydro-19(R)-19-hydroxy-9-deoxo-9-methylene-15(S)-15-methyl-PGE$_1$,
2-decarboxy-2-tetrazolyl-2,3-didehydro-19(R)-19-hydroxy-9-deoxo-9-methylene-11-deoxy-PGE$_1$,
2-decarboxy-2-tetrazolyl-2,3-didehydro-19(R)-19-hydroxy-9-deoxo-9-methylene-11-deoxy-16,16-difluoro-PGE$_1$,
2-decarboxy-2-tetrazolyl-2,3-didehydro-19(R)-19-hydroxy-9-deoxo-9-methylene-11-deoxy-15(S)-15-methyl-PGE$_1$,
2-decarboxy-2-tetrazolyl-19(R)-19-hydroxyPGF$_{1α}$,
2-decarboxy-2-tetrazolyl-16,16-dimethyl-19(R)-19-hydroxy-PGF$_{xzl}$,
2-decarboxy-2-tetrazolyl-16,16-difluoro-19(R)-19-hydroxy-PGF$_{1α}$,
2-decarboxy-2-tetrazolyl-13,14-dihydro-19(R)-19-hydroxy-PGF$_{1α}$,
2-decarboxy-2-tetrazolyl-11-deoxy-19(R)-19-hydroxy-PGF$_{1α}$,
2-decarboxy-2-tetrazolyl-11-deoxy-16,16-dimethyl-19(R)-19-hydroxy-PGF$_{1α}$,
2-decarboxy-2-tetrazolyl-11-deoxy-16,16-difluoro-19(R)-19-hydroxy-PGF$_{1α}$,
2-decarboxy-2-tetrazolyl-11-deoxy-13,14-dihydro-19(R)-19-hydroxy-PGF$_{1α}$,
2-decarboxy-2-tetrazolyl-11-deoxy-11α-hydroxymethyl-19(R)-19-hydroxy-PGF$_{1α}$,
2-decarboxy-2-tetrazolyl-11-deoxy-11α-hydroxymethyl-16,16-dimethyl-19(R)-19-hydroxy-PGF$_{1α}$,
2-decarboxy-2-tetrazolyl-11-deoxy-11α-hydroxymethyl-16,16-difluoro-19(R)-19-hydroxy-PGF$_{1α}$,
2-decarboxy-2-tetrazolyl-11-deoxy-11α-hydroxymethyl-13,14-dihydro-19(R)-19-hydroxy-PGF$_{1α}$,
2-decarboxy-2-tetrazolyl-19(R)-19-hydroxy-PGF$_{1β}$,
2-decarboxy-2-tetrazolyl-16,16-dimethyl-19(R)-19-hydroxy-PGF$_{1β}$,
2-decarboxy-2-tetrazolyl-16,16-difluoro-19(R)-19-hydroxy-PGF$_{1β}$,
2-decarboxy-2-tetrazolyl-13,14-dihydro-19(R)-19-hydroxy-PGF$_{2β}$,
2-decarboxy-2-tetrazolyl-11-deoxy-19(R)-19-hydroxy-PGF$_{1β}$,
2-decarboxy-2-tetrazolyl-11-deoxy-16,16-dimethyl-19(R)-19-hydroxy-PGF$_{1β}$,
2-decarboxy-2-tetrazolyl-16,16-difluoro-19(R)-19hydroxy-PGF$_{1β}$,
2-decarboxy-2-tetrazolyl-11-deoxy-13,14-dihydro-19(R)-19-hydroxy-PGF$_{1β}$,
2-decarboxy-2-tetrazolyl-11-deoxy-11α-hydroxymethyl-19(R)-19-hydroxy-PGF$_{1β}$,
2-decarboxy-2-tetrazolyl-11-deoxy-11α-hydroxymethyl-16,16-dimethyl-19(R)-19-hydroxy-PGF$_{1β}$,
2-decarboxy-2-tetrazolyl-11-deoxy-11α-hydroxymethyl-16,16-difluoro-19(R)-19-hydroxy-PGF$_{1β}$,
2-decarboxy-2-tetrazolyl-11-deoxy-11α-hydroxymethyl-13,14-dihydro-19(R)-19-hydroxy-PGF$_{1β}$,
2-decarboxy-2-tetrazolyl-19(R)-19-hydroxy-PGE$_1$,
2-decarboxy-2-tetrazolyl-16,16-dimethyl-19(R)-19-hydroxy-PGE$_1$,
2-decarboxy-2-tetrazolyl-16,16-difluoro-19(R)-19-hydroxy-PGE$_1$,
2-decarboxy-2-tetrazolyl-13,14-dihydro-19(R)-19-hydroxy-PGE$_1$,
2-decarboxy-2-tetrazolyl-11-deoxy-19(R)-19-hydroxy-PGE$_1$,
2-decarboxy-2-tetrazolyl-11-deoxy-16,16-dimethyl-19(R)-19-hydroxy-PGE$_1$,
2-decarboxy-2-tetrazolyl-11-deoxy-16,16-difluoro-19(R)-19-hydroxy-PGE$_1$,
2-decarboxy-2-tetrazolyl-11-deoxy-13,14-dihydro-19(R)-19-hydroxy-PGE$_1$,
2-decarboxy-2-tetrazolyl-11-deoxy-11α-hydroxymethyl-19(R)-19-hydroxy-PGE$_1$,
2-decarboxy-2-tetrazolyl-11-deoxy-11α-hydroxymethyl-16,16-dimethyl-19(R)-19-hydroxy-PGE$_1$,
2-decarboxy-2-tetrazolyl-11-deoxy-11α-hydroxymethyl-16,16-difluoro-19(R)-19-hydroxy-PGE$_1$,
2-decarboxy-2-tetrazolyl-11-deoxy-11α-hydroxymethyl-13,14-dihydro-19(R)-19-hydroxy-PGE$_1$,
2-decarboxy-2-tetrazolyl-9-deoxo-9-methylene-19(R)-19-hydroxy-PGE$_1$,
2-decarboxy-2-tetrazolyl-9-deoxo-9-methylene-16,16-dimethyl-19(R)-19-hydroxy-PGE$_1$,
2-decarboxy-2-tetrazolyl-9-deoxo-9-methylene-16,16-difluoro-19(R)-19-hydroxy-PGE$_1$,
2-decarboxy-2-tetrazolyl-9-deoxo-9-methylene-13,14dihydro-19(R)-19-hydroxy-PGE$_1$,
2-decarboxy-2-tetrazolyl-9-deoxo-9-methylene-11-deoxy-19(R)-19-hydroxy-PGE$_1$,
2-decarboxy-2-tetrazolyl-9-deoxo-9-methylene-11-deoxy-16,16-dimethyl-19(R)-19-hydroxy-PGE$_1$,
2-decarboxy-2-tetrazolyl-9-deoxo-9-methylene-1-deoxy-16,16-difluoro-19(R)-19-hydroxy-PGE$_1$,
2-decarboxy-2-tetrazolyl-9-deoxo-9-methylene-11-deoxy-13,14-dihydro-19(R)-19-hydroxy-PGE$_1$,
2-decarboxy-2-tetrazolyl-9-deoxo-9-methylene-11-deoxy-11α-hydroxymethyl-19(R)-19-hydroxy-PGE$_1$,
2-decarboxy-2-tetrazolyl-9-deoxo-9-methylene-11-deoxy-11α-hydroxymethyl-16,16-dimethyl-19(R)-19-hydroxy-PGE$_1$,
2-decarboxy-2-tetrazolyl-9-deoxo-9-methylene-11-deoxy-11α-hydroxymethyl-16,16-difluoro-19(R)-19-hydroxy-PGE$_1$,
2-decarboxy-2-tetrazolyl-9-deoxo-9-methylene-11-deoxy-11α-hydroxymethyl-13,14-dihydro-19(R)-19-hydroxy-PGE$_1$, The compounds of the present invention are particularly useful for inducing prostaglandin-like biological effects, as is described in U.S. Ser. No. 025,899. Uses of compounds in accordance with the present invention include, therefore, anti-asthmatic indications.

I claim:
1. A compound of the formula

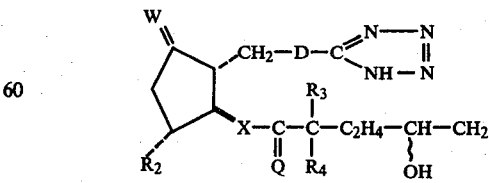

wherein
D is
(1) cis—CH=CH—CH$_2$—(CH$_2$)$_g$—CH$_2$—,
(2) cis—CH=CH—CH$_2$—(CH$_2$)$_g$—CF$_2$—, (3) cis—$CH_2$—CH=CH—$CH_2$—$CH_2$—,
(4) trans—$(CH_2)_3$—CH=CH—,
(5) —$(CH_2)_3$—$(CH_2)_g$—$CH_2$—,
(6) —$(CH_2)_3$—$CH_2$—$CF_2$—,
(7) —$(CH_2)_3$—O—$CH_2$—,
(8) —$(CH_2)_2$—O—$(CH_2)_2$—,
(9) —$CH_2$—O—$(CH_2)_3$—,
(10) —(m—ph)—$(CH_2)_2$—, or
(11) —(m—ph)—O—$CH_2$— wherein m—ph is inter-meta-phenylene, and wherein g is zero, one, two, or three;

wherein Q is $\alpha$—OH:$\beta$—$R_5$ or $\alpha$—$R_5$:$\alpha$—OH, wherein $R_5$ is hydrogen or methyl, wherein $R_2$ is hydrogen, hydroxyl, or hydroxymethyl;

wherein $R_3$ and $R_4$ are hydrogen, methyl, or fluoro, being the same or different, with the proviso that one of $R_3$ and $R_4$ is fluoro only when the other is hydrogen or fluoro;

wherein W is oxo, methylene, $\alpha$—OH:$\beta$—H, or $\alpha$—H:$\beta$—OH;

and wherein X is cis- or trans-CH=CH—, —C≡C—, or —$CH_2CH_2$—.

* * * * *